United States Patent [19]
King

[11] Patent Number: 4,886,808
[45] Date of Patent: Dec. 12, 1989

[54] INDAZOLYL CARBOXYLIC ACID AMIDES USEFUL FOR TREATING MIGRAINE CLUSTERS HEADACHE, TRIGEMINAL NEURALGIA OR EMESIS

[75] Inventor: Francis D. King, Bishop's Stortford, England

[73] Assignee: Beecham Group p.l.c., Brentford, England

[21] Appl. No.: 171,141

[22] Filed: Mar. 16, 1988

Related U.S. Application Data

[63] Continuation of Ser. No. 856,452, Apr. 25, 1986.

[30] Foreign Application Priority Data

Apr. 27, 1985 [GB] United Kingdom ................. 8510752
Oct. 21, 1985 [GB] United Kingdom ................. 8525913

[51] Int. Cl.⁴ ................. C07D 403/12; A61K 31/415; A61K 31/445
[52] U.S. Cl. .................... 514/299; 514/304; 546/112; 546/126; 548/372
[58] Field of Search ................. 514/299, 304; 546/122, 546/126

[56] References Cited
FOREIGN PATENT DOCUMENTS

| | | | |
|---|---|---|---|
| 770068 | 11/1971 | Belgium | 548/373 |
| 0214772 | 3/1987 | European Pat. Off. | 546/133 |
| 2548666 | 1/1985 | France | 546/124 |
| 8400166 | 1/1984 | PCT Int'l Appl. | 546/133 |
| 8501038 | 3/1985 | PCT Int'l Appl. | 546/133 |
| 2100259 | 12/1982 | United Kingdom | 546/126 |
| 2125398 | 3/1984 | United Kingdom | 546/127 |
| 2145416 | 3/1985 | United Kingdom | 546/126 |

OTHER PUBLICATIONS

World Patents Index (Derwent) Accession No. 85-045742/08 (Feb. 1984).
P. Fludzinski et al., "Indazoles as Indole Bioisosteres: Synthesis and Evaluation of the Tropanyl Ester and Amide of Indazole-3-Carboxylate as Antagonists at the Serotonin 5HT₃ Receptor", *J. Medicinal Chem.*, 30(9), pp. 1535-1537 (1987).
"5HT₃-Antagonists in Anxiety and Szhizophrenia", *SCRIP*, No. 1264, Dec. 9, 1987, p. 23.

*Primary Examiner*—Alan L. Rotman
*Attorney, Agent, or Firm*—James F. Haley, Jr.; David K. Barr; Emily A. Evans

[57] ABSTRACT

Compounds of formula (I) and pharmaceutically acceptable salts thereof:

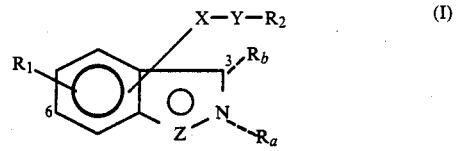

wherein
X is CO and Y is NH;
Z is $NR_3$ wherein $R_3$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and $R_a$ is not present; or
Z is N and $R_a$ is as defined for $R_3$ above;
$R_b$ is present when $X$-$Y$-$R_2$ is attached at the phenyl ring and is selected from hydrogen, halogen, $CF_3$, hydroxy, $C_{1-6}$ alkoxy or $C_{1-6}$ alkyl;
$R_1$ is hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, $N(C_{1-6}$ alkylsulphonyl)-$N$-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;
$R_2$ is a group of formula (a)

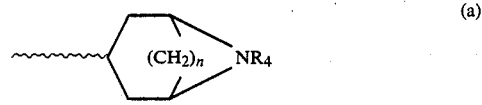

wherein n is 2 or 3; and
$R_4$ is $C_{1-7}$ alkyl, $C_{3-8}$ cycloalkyl, $C_{3-8}$ cycloalkyl-$C_{1-2}$ alkyl, or a group $(CH_2)_tR_6$ where t is 1 or 2 and $R_6$ is thienyl, pyrrolyl or furyl optionally substituted by one or two substituents selected from $C_{1-6}$ alkyl, $C_{1-6}$ alkoxy, trifluoromethyl or halogen, or is phenyl optionally substituted by one or two substituents having 5-HT antagonist activity and/or gastric motility enhancing activity.

20 Claims, No Drawings

INDAZOLYL CARBOXYLIC ACID AMIDES USEFUL FOR TREATING MIGRAINE CLUSTERS HEADACHE, TRIGEMINAL NEURALGIA OR EMESIS

This is a continuation, of application Ser. No. 856,452, filed Apr. 25, 1986.

This invention relates to novel compounds having useful pharmacological properties, to pharmaceutical compositions containing them, to a process and intermediates for their preparation, and to their use as pharmaceuticals.

UK Patent Applications, GB Nos. 2100259A and 2125398A describe benzoates and benzamides having an azabicyclic side chain and possessing 5-HT (5-Hydroxytryptamine) antagonist activity.

A class of novel, structurally distinct compounds has now been discovered. These compounds have 5-HT antagonist activity and/or gastric motility enhancing activity.

Accordingly, the present invention provides a compound of formula (I), or a pharmaceutically acceptable salt thereof:

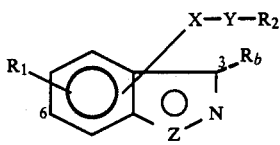

wherein

X is CO and Y is NH or O, or X is NH and Y is CO;
Z is $CH_2$, O, S or $NR_3$ wherein $R_3$ is hydrogen, $C_{1-6}$ alkyl, $C_{3-7}$ alkenyl-methyl, phenyl or phenyl $C_{1-4}$ alkyl either of which phenyl moieties may be substituted by one or two of halogen, $CF_3$, $C_{1-6}$ alkoxy or $C_{1-6}$ alkyl; and
$R_b$ is present when X-Y-$R_2$ is attached at the phenyl ring and is selected from hydrogen, halogen, $CF_3$, hydroxy, $C_{1-6}$ alkoxy or $C_{1-6}$ alkyl;
$R_1$ is hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonylamino, N-($C_{1-6}$ alkylsulphonyl)-N-$C_{1-4}$ alkylamino, $C_{1-6}$ alkylsulphinyl, hydroxy, nitro or amino, aminocarbonyl, aminosulphonyl, aminosulphonylamino or N-(aminosulphonyl)-$C_{1-4}$ alkylamino optionally N-substituted by one or two groups selected from $C_{1-6}$ alkyl, $C_{3-8}$ cycloalkyl, $C_{3-8}$ cycloalkyl $C_{1-4}$ alkyl, phenyl or phenyl $C_{1-4}$ alkyl groups or optionally N-disubstituted by $C_{4-5}$ polymethylene;
$R_2$ is a group of formula (a), (b) or (c)

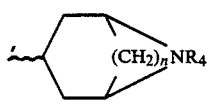

(a)

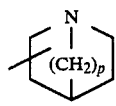

(b)

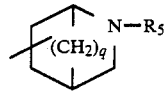

(c)

wherein n is 2 or 3; p and q are independently 1 to 3; and
$R_4$ or $R_5$ is $C_{1-7}$ alkyl, $C_{3-8}$ cycloalkyl, $C_{3-8}$ cycloalkyl-$C_{1-2}$ alkyl, or a group $(CH_2)_tR_6$ where t is 1 or 2 and $R_6$ is thienyl, pyrrolyl or furyl optionally substituted by one or two substituents selected from $C_{1-6}$ alkyl, $C_{1-6}$ alkoxy, trifluoromethyl or halogen, or is phenyl optionally substituted by one or two substituents selected from $C_{1-4}$ alkoxy, trifluoromethyl, halogen, nitro, carboxy, esterified carboxy, and $C_{1-4}$ alkyl optionally substituted by hydroxy, $C_{1-4}$ alkoxy, carboxy, esterified carboxy or in vivo hydrolysable acyloxy.

Preferably X is CO and Y is NH or O.

Z is often $NR_3$.

Suitable values for $R_3$ include hydrogen, methyl, ethyl, n- and iso-propyl; prop-2-enyl, but-2-enyl, but-3-enyl, 1-methylenepropyl and 1-methylprop-2-yl in their E and Z forms where stereoisomerism exists, phenyl and benzyl optionally substituted by one or two of chloro, bromo, $CF_3$, methoxy, ethoxy, n- and iso-propoxy, methyl, ethyl, n- and iso-propyl. Preferably $R_3$ is hydrogen or methyl, most preferably methyl.

Suitable values for $R_b$ when present include hydrogen, chloro, bromo, $CF_3$, methoxy, ethoxy, n- and iso-propoxy, methyl, ethyl, n- and iso-propyl.

Often the X-Y-$R_2$ side chain is attached at positions 3 or 6, as depicted in formula (I), preferably position 3.

Values for $R_1$ include hydrogen, fluoro, chloro, bromo, $CF_3$, methyl, ethyl, methoxy, ethoxy, methylthio, ethylthio, acetyl, propionyl, acetylamino, methylsulphonylamino, methylsulphinyl, hydroxy, nitro; and amino, amino carbonyl, aminosulphonyl, aminosulphonylamino or N-(aminosulphonyl)-methylamino any of which may be optionally substituted by one or two methyl groups or by a cyclopentyl or cyclohexyl group or disubstituted by $C_4$ or $C_5$ polymethylene; $R_1$ is often hydrogen or 5-halo, such as 5-fluoro or 5-chloro.

Preferably p and q are 1 or 2.

Preferably $R_4/R_5$ is $C_{1-7}$ alkyl, including as groups of interest, $C_{1-3}$ alkyl such as methyl, ethyl and n- and iso-propyl. Within $C_{1-7}$ alkyl, $C_{4-7}$ alkyl are also of interest, especially those of the formula $(CH_2)uR_9$ wherein u is 1 or 2 and $R_9$ is a secondary or tertiary $C_{3-6}$ alkyl group. Examples of $C_{4-7}$ alkyl include n-, sec- and tert-butyl, n-pentyl, n-heptyl, and iso-butyl, 3-methylbutyl, and tert-butylmethyl. $R_4/R_5$ is preferably methyl or ethyl, most preferably methyl.

Examples of $R_4/R_5$ when $C_{3-8}$ cycloalkyl-$C_{1-2}$ alkyl include in particular those wherein the cycloalkyl moiety is cyclohexyl or cyclopropyl.

Examples of $R_4/R_5$ include cyclopropylmethyl, cyclobutylmethyl, cyclopentylmethyl, cyclohexylmethyl, cyclopropylethyl, cyclobutylethyl, cycloentylethyl, cyclohexylethyl, tert-butylmethyl, iso-propylmethyl, iso-propylethyl and tert-butylethyl.

$R_4/R_5$ may in particular be cyclopropylmethyl, cyclohexylmethyl, iso-propylmethy, tert-butylmethyl or iso-propylethyl, preferably tert-butylmethyl.

Examples of $R_4/R_5$, when -$(CH_2)_tR_6$, are those wherein t is 1. $R_6$ may be 2- or 3-thienyl, 2- or 3- pyrrolyl or 2- or 3-furyl optionally substituted by one of $C_{1-4}$ alkyl, $C_{1-4}$ alkoxy, trifluoromethyl or halogen, or preferably is phenyl optionally substituted by one of $C_{1-4}$ alkyl, trifluoromethyl, halogen, carboxy, esterified carboxy and $C_{1-4}$ alkyl optionally substituted by hydroxy, $C_{1-4}$ alkoxy, carboxy, esterified carboxy and in vivo hydrolysable acyloxy.

The following five paragraphs relate to substituents of $R_6$ groups as appropriate.

Examples of $C_{1-4}$ alkoxy substituents include methoxy, ethoxy and n- and iso-propoxy, in particular methoxy.

Examples of halogen substituents include fluoro, chloro and bromo, often in the 3-or 4- position, in particular chloro.

In optionally substituted $C_{1-4}$ alkyl substituents, examples of $C_{1-4}$ alkyl include methyl, ethyl, n- and iso-propyl, and n- and iso-, sec- and tert-butyl; methyl however is preferred. Examples of substituents of such alkyl groups include hydroxy, methoxy, ethoxy, n- and iso-propoxy, carboxy, esterified carboxy and in vivo hydrolysable acyloxy. The substitution preferably occurs on the terminal carbon atom of the alkyl group.

Examples of esterified carboxy groups include $C_{1-4}$ alkoxycarbonyl, such as methoxy-, ethoxy-, n- and iso-propoxycarbonyl, or phenoxycarbonyl or benzyloxycarbonyl optionally substituted in the phenyl ring by one or two substituents selected from $C_{1-4}$ alkyl, $C_{1-4}$ alkoxy, trifluoromethyl, halogen or nitro.

Examples of in vivo hydrolysable acyloxy groups include $C_{1-6}$ alkanoyloxy, for example acetoxy, propionoxy, n- and iso-butyroxy, and 2,3-dimethylpropanoyloxy, benzoyloxy or benzenesulphonyloxy either being optionally substituted in the phenyl ring by one or two substituents selected from $Cl_4$ alkyl, $C_{1-4}$ alkoxy, trifluoromethyl, halogen or nitro, or sulphonyloxy groups, for example $C_{1-6}$ alkanesulphonyloxy group, such as methanesulphonyloxy.

Examples of $R_4/R_5$, when $-(CH_2)_tR_6$, are those wherein t is 1 and $R_6$ is unsubstituted phenyl or mono-substituted phenyl. Examples of substituents include methyl, trifluoromethyl, fluoro, chloro and bromo.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Examples of pharmaceutically acceptable salts include quaternary derivatives of the compounds of formula (I) such as the compounds quaternised by compounds $R_{10}$-T wherein $R_{10}$ is $C_{1-6}$ alkyl, phenyl-$C_{1-6}$ alkyl or $C_{5-7}$ cycloalkyl, and T is a radical corresponding to an anion of an acid. Suitable examples of $R_{10}$ include methyl, ethyl and n- and iso-propyl; and benzyl and phenethyl. Suitable examples of T include halides such as chloride, bromide and iodide.

Examples of pharmaceutically acceptable salts of the compounds of formula (I) also form internal salts such as pharmaceutically acceptable N-oxides.

The compounds of the formula (I) and their pharmaceutically acceptable salts, (including quaternary derivatives and N-oxides) may also form pharmaceutically acceptable solvates, such as hydrates, which are included whenever such compounds and salts are herein referred to.

It will of course be realised that some of the compounds of the formula (I) have chiral or prochiral centres and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods.

It will also be realised that compounds of the formula (I) wherein $R_3$ is hydrogen can exist as two tautomeric forms i.e. that wherein $R_3$ is hydrogen and that wherein the hydrogen is attached to the indazole nitrogen at position 2 and Z is N. The invention extends to each of these forms and to mixtures thereof. The predominant tautomeric form is usually that wherein $R_3$ is hydrogen.

A group of compounds within formula (I) is of formula (II):

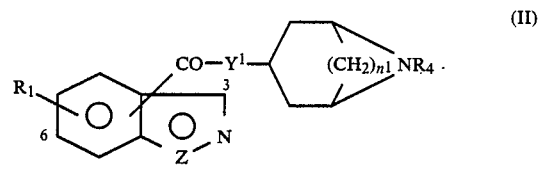

wherein $n^1$ is 2 or 3, $Y^1$ is NH or O and the remaining variables are as defined in formula (I).

Examples of the variables and preferred variables are as so described for corresponding variables in relation to formula (I).

A further group of compounds within formula (I) is of formula (III):

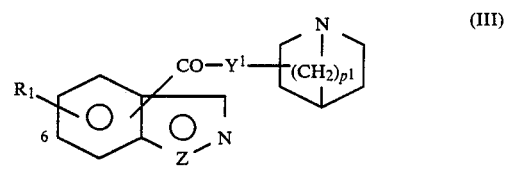

wherein $p^1$ is 1 or 2 and the remaining variables are as defined in formulae (I) and (II).

Examples of the variables and preferred variables are as so described for the corresponding variables in formula (I).

There is a further group of compounds within formula (I) of formula (IV):

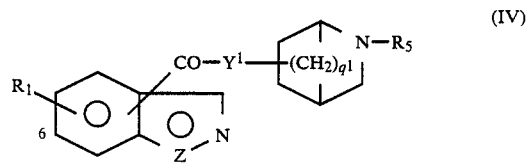

wherein $q^1$ is 1 or 2 and the remaining variables are as defined in formulae (I) and (II).

Examples of the variables and preferred variables are so described as the corresponding variables in formula (I).

The invention also provides a process for the preparation of a compound of formula (I), or a pharmaceutically acceptable salt thereof, which process comprises reacting a compound of formula (V):

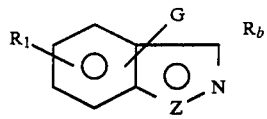

(V)

with a compound of formula (VI):

$LR_2$ (VI)

wherein

G is $COQ_1$ where $Q_1$ is a group displaceable by a nucleophile, and L is $NH_2$ or OH or a reactive derivative thereof and the remaining variables are as hereinbefore defined; and thereafter optionally converting any $R_1$, $R_3$, $R_4$, $R_5$, and $R_b$ group to another $R_1$, $R_3$, $R_4$, $R_5$, or $R_b$ group respectively, and optionally forming a pharmaceutically acceptable salt of the resultant compound of formula (I).

Examples of leaving groups $Q_1$, displaceable by a nucleophile include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy. Alternatively, when G is $COQ_1$ and Z is NH in formula (V), a nitrogen heterocycle may act as the leaving group i.e. that obtained by reaction of a compound of formula (V) wherein G is $CO_2H$ and Z is NH with thionyl chloride to give a diindazolo [2,3-a,2'3'-d]pyrazine-7,14-dione.

If a group $Q_1$ is a halide, then the reaction is preferably carried out at non-extreme temperatures in an inert non-hydroxylic solvent, such as benzene, dichloromethane, toluene, diethyl ether, THF (tetrahydrofuran) or DMF (dimethylformamide). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°-100° C., in particular 10°-80° C. are suitable.

If a group $Q_1$ is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide. When Y is CO the compound of formula (IV) is preferably in the form of an acid addition salt, such as the hydrohalide, for example the hydrochloride. The reaction may be carried out at any non-extreme temperature, such as −10° to 100° C., for example, 0° to 80° C. Generally, higher reaction temperatures are employed with less active compounds whereas lower temperatures are employed with the more active compounds.

If a group $Q_1$ is carboxylic acyloxy, then the reaction is preferably carried in substantially the same manner as the reaction when $Q_1$ is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein $Q_1$ is hydroxy with a $C_{1-4}$ alkyl chloroformate.

If a group $Q_1$ is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When the leaving group $Q_1$ is a nitrogen heterocycle as hereinbefore described the reaction is carried out in a similar manner as when $Q_1$ is a halide.

When L is OH or a reactive derivative thereof, the reactive derivative is often a salt, such as the lithium salt.

Pharmaceutically acceptable salts of the compounds of this invention may be formed conventionally.

The salts may be formed for example by reaction of the base compound of formula (I) with a pharmaceutically acceptable organic or inorganic acid.

It will be apparent that compounds of the formula (I) containing an $R_1$, $R_3$, $R_4$, $R_5$, or $R_b$ group which is convertible to another $R_1$, $R_3$, $R_4$, $R_5$, or $R_b$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a $C_{1-7}$ acylamino substituent is convertible to an amino substituent by deacylation;

(iv) an amino substituent is convertible to a $C_{1-4}$ acylamino substituent by acylation with a carboxylic acid derivative;

(v) a hydrogen substituent is convertible to a halogen substituent by halogenation;

(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;

(vii) an amino, aminocarbonyl, aminosulphonyl, aminosulphonylamino or N-(aminosulphonyl)-N-$C_{1-4}$ alkylamino substituent is convertible to a corresponding substituent substituted by one or two groups selected from $C_{1-6}$ alkyl, $C_{3-8}$ cycloalkyl, $C_{1-4}$ alkyl or phenyl $C_{1-4}$ alkyl groups any of which phenyl groups may be substituted by one or more groups selected from halogen, trifluoromethyl, $C_{1-6}$ alkyl, $C_{1-6}$ alkoxy and nitro, or disubstituted by $C_{4-5}$ polymethylene, by N-alkylation;

(viii) an amino substituent is convertible to a $C_{1-6}$ alkylsulphonylamino group or an aminosulphonylamino group optionally N-substituted as defined by acylation with a $C_{1-6}$ alkylsulphonyl chloride or di-substituted aminosulphonyl chloride.

(ix) A $C_{1-4}$ alkylamino substituent group is convertible to a N-($C_{1-6}$ alkylsulphonyl)N-$C_{1-4}$ alkylamino group or an N-(amino sulphonyl)N-$C_{1-4}$ alkylamino group optionally N-substituted as defined by acylation with a $C_{1-6}$ alkylsulphonyl chloride or di-substituted aminosulphonyl chloride.

Conversions (i) to (ix) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv), (viii), and (ix) the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise the N- moiety of a side chain (a), (b) or (c) and suitable precautions will routinely be taken by the skilled man.

In regard to (vii), alkylation is carried out with a corresponding alkylating agent such as the chloride or bromide under conventional conditions.

$R_4/R_5$ optionally substituted benzyl as hereinbefore defined may be replaced by other $R_4/R_5$. Such benzyl groups may, for example, be removed, when $R_1$ or $R_b$ is not halogen, by conventional transition metal catalysed hydrogenolysis to give compounds of the formula (VII):

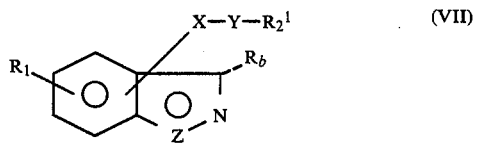

wherein $R_2^1$ is of formula (d) or (e)

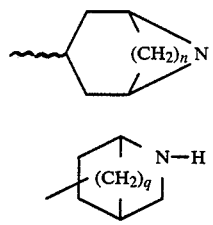

wherein the variables are as defined in formula (I).

This invention also provides a further process for the preparation of a compound of the formula (I) wherein $R_2$ is of formula (a) or (c), which comprises N-alkylating a compound of formula (VII), and optionally forming a pharmaceutically acceptable salt, of the resulting compound of the formula (I).

In this further process of the invention 'N-alkylation' comprises the substitution of the N-atom depicted in formula (VII) by any group $R_4/R_5$ as hereinbefore defined. This may be achieved by reaction of the compound of formula (VII) with a compound $R_4Q_2$ or $R_5Q_2$ wherein $R_4$ and $R_5$ are as hereinbefore defined and $Q_2$ is a leaving group.

Suitable values for $Q_2$ include groups displaced by nucleophiles such as Cl, Br, I, $OSO_2CH_3$ or $OSO_2C_6H_4pCH_3$.

Favoured values for $Q_2$ include Cl, Br and I.

The reaction may be carried out under conventional alkylation conditions for example in an inert solvent such as dimethylformamide in the presence of an acid acceptor such as potassium carbonate. Generally the reaction is carried out at non-extreme temperature such as at ambient or slightly above.

Alternatively, 'N-alkylation' may be effected under conventional reductive alkylation conditions when the group $R_4$ or $R_5$ in the compound of formula (I) contains a methylene group adjacent to the N-atom in the bicycle.

Interconverting $R_4$ or $R_5$ in the compound of the formula (VII) before coupling with the compound of the formula (V) is also possible. Such interconversions are effected conveniently under the above conditions. It is desirable to protect any amine function with a group readily removable by acidolysis such as a $C_{2-7}$ alkanoyl group, before $R_4/R_5$ interconversion.

The substituents in the phenyl ring when $R_4$ or $R_5$ is benzyl in a compound of formula (I), in particular the substituted $C_{1-4}$ alkyl substituents, are interconvertible. A number of such interconversions are possible not only for the end compounds of formula (I), but also for their intermediates as follows:

(i) a carboxy $C_{1-4}$ alkyl substituent is convertible to an esterified carboxy $C_{1-4}$ alkyl substituent by esterification;

(ii) an esterified carboxy $C_{1-4}$ alkyl substituent is convertible to a carboxy $C_{1-4}$ alkyl substituent by deesterification;

(iii) an $C_{1-4}$ alkoxy $C_{1-4}$ alkyl substituent or an in vivo hydrolysable $C_{2-4}$ acyloxy $C_{1-4}$ alkyl substituent is convertible to an hydroxy $C_{1-4}$ alkyl substituent by de-etherification;

(iv) an optionally esterified carboxy or carboxy $C_{1-3}$ alkyl substituent is convertible to an hydroxymethyl or hydroxy $C_{2-4}$ alkyl substituent by reduction; and (v) a hydroxy $C_{1-4}$ alkyl substituent is convertible to $C_{1-4}$ alkoxy $C_{1-4}$ alkyl by O-alkylation or to in vivo hydrolysable $C_{1-4}$ acyloxy $C_{1-4}$ alkyl by O-acylation.

Conversions (i) to (v) are only exemplary and are not exhaustive of the possibilities.

In regard to (i) and (ii), the esterification and deesterification reactions are carried out in conventional manner.

In regard to (iii), a $C_{1-4}$ alkoxy $C_{1-4}$ alkyl substituent is convertible to an hydroxy $C_{1-4}$ alkyl substituent by conventional methods, such as warming with aqueous hydrobromic acid or by treatment with pyridine hydrochloride, boron tribromide, boron triiodide or iodotrimethylsilane.

An in vivo hydrolysable $C_{2-4}$ acyloxy $C_{1-4}$ alkyl substituent is convertible to an hydroxy $C_{1-4}$ alkyl substituent by acid or base hydrolysis.

In regard to (iv), the reduction is carried out with a selective metal complex hydride, for example lithium aluminium hydride, under conventional conditions.

In regard to (v), O-alkylation is carried out under conventional conditions in an inert solvent at a non-extreme temperature such as ambient temperature or slightly above or at reflux temperature. The $C_{1-4}$ alkylating agent has a leaving group that is readily displaceable by a nucleophile. Examples of leaving groups include halide, such as chloride, bromide or iodide, or labile acyloxy groups, such as mesyl and tosyl.

O-acylation is carried out under conventional conditions with an acylating agent which has an acyl group capable of forming an in vivo hydrolysable acyloxy group and leaving group, such as halide, for example chloride and bromide, and hydrogen. When halide is the leaving group, the reaction is generally carried out in the presence of a base. When hydroxy is the leaving group, the reaction is generally carried out in the presence of a dehydrating agent, such as dicyclohexylcarbodiimide, in an inert solvent at non-extreme temperature, such as ambient temperature or slightly above, or reflux temperature.

Before carrying out any of these conversions, the effect, if any, on other substituents should be considered, and such reagents as are appropriate should be selected together with the adoption of such precautionary measures as are necessary. For example, O-alkylation and O-acylation may also produce N-alkylated and N-acylated products respectively unless the nitrogen atom(s) is (are) previously protected. This may be conveniently achieved by carrying out the alkylation or acylation reaction in a strong acid, such as trifluoroacetic acid, which protonates, and thereby protects, the nitrogen atom(s).

When $R_4$ or $R_5$ in the compound of formula (VI) contains a methylene group adjacent to the N-atom in the bicycle it is often convenient in the preparation of such a compound of formula (VI) to prepare the corresponding compound wherein the methylene group is replaced by —CO—, or for $R_4$ or $R_5$ is methyl, where the methyl group is replaced by esterified carboxyl. Such compounds may then be reduced using a strong reductant such as lithium aluminium hydride to the corresponding compound of formula (V).

The compounds of formula (V) and (I) are known or are preparable analogously to, or routinely from, known compounds.

Compounds of the formula (VI) wherein $R_2$ is of formula (c) may be prepared as described in European Patent Publication No. EP-A-115933 or by analogous methods thereto.

Compounds of the formula (VII) are novel and form an aspect of the invention.

It will be realised that in the compound of the formula (I) the -X-Y-linkage may have an endo or exo orientation with respect to the ring of the bicyclic moiety to which it is attached. A mixture of endo and exo isomers of the compound of the formula (I) may be synthesised non-stereospecifically and the desired isomer separated conventionally therefrom e.g. by chromatography; or alternatively the endo and exo isomer may if desired by synthesised from the corresponding isomer of the compound of the formula (VI).

The compounds of the present invention are 5-HT antagonists and it is thus believed may generally be used in the treatment or prophylaxis of migraine, cluster headaches and trigeminal neuralgia; and also as anti-emetics, in particular that of preventing vomiting and nausea associated with cancer therapy, and motion sickness. Examples of such cancer therapy include that using cytotoxic agents, such as cisplatin, doxorubicin and cyclophosphamide, particularly cisplatin; and also radiation treatment. Compounds which are 5-HT antagonists may also be of potential use in the treatment of CNS disorders such as anxiety and psychosis; arrythmia, obesity and irritable bowel syndrome.

The compounds of the present invention also have gastric motility enhancing activity, useful in the treatment of disorders such as retarded gastric emptying, dyspepsia, flatulence, oesophagal reflux and peptic ulcer.

The invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylceluulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment prophylaxis of migraine, cluster headache, trigeminal neuralgia and/or emesis in mammals, such as humans, which comprises the administration to the mammal of an effective amount of a compound of the formula (I) or a pharmaceutically acceptable salt thereof.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 1000 mg for example 1 to 500 mg, of the compound of the invention. Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of migraine, cluster headache, trigeminal neuralgia and/or emesis.

The following Examples illustrate the preparation of compounds of formula (I).

N.B. Nomenclature is based on Chemical Abstracts Index Guide 1977 published by the American Chemical Society.

EXAMPLE 1

3-Indazolecarboxylic acid (endo-8-methyl-8-azabiclo[3.2.1]oct-3-yl)ester (E1)

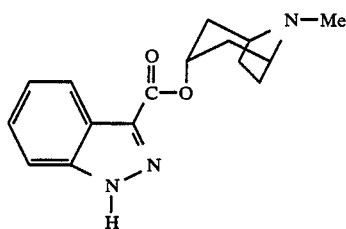

A solution of tropine (0.45 g) and KBu$^t$O (0.36 g) in amine-free DMF (50 ml) was stirred at room temperature for 30 min. The more volatile t-butanol was removed by rotary evaporation and the residual solution treated with diinazolo[2,3-a 2',3'-d]-pyrazine-7,14-dione (0.2 g). After heating to 120° for 2 h, the reaction mixture was cooled, evaporated to dryness and the residue treated with saturated NaHCO$_3$ solution (50 ml). The pH was adjusted to ca.8 with acetic acid and the product extracted into CHCl$_3$ (3×100 ml). The organic extracts were dried (Na$_2$SO$_4$), evaporated to dryness and the residue triturated with diethylether to give E1 (0.16 g) mp 234°–235° (dec).

$^1$H NMR (270 MHz, d$_6$-DMSO), δ 13.5 (1H, brs), 8.18 (1H, d), 7.60 (1H, d), 7.39 (1H, t) 7.28 (1H, t), 5.31 (1H, t), 3.23 (2H, brs), 2.36 (3H, s), 2.45–1.90 (8H, m).

EXAMPLE 2

N-(Endo-9-methyl-9-azabicyclo[3,3,1]non-3-yl)indazole-3-carboxamide (E2)

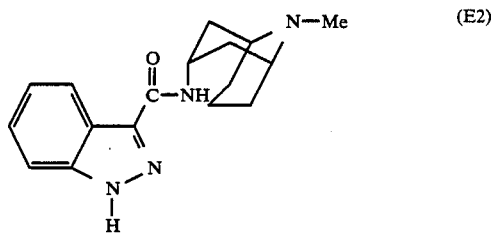

A suspension of diindazolo[2,3-a,2',3'-d)pyrazin-7,14-dione (0.76 g) in DMF (20 ml) was heated with endo-9-methyl-9-azabicyclo[3,3,1]nonan-3-amine (0.31 g) for 2 h at 100° C. After evaporation to dryness, the residue was purified by column chromatography (TLC grade alumina, CHCl$_3$) to give the title compound (E2) (0.12 g) m.p. 209°–212° C.

$^1$H NMR (270 MHz, CDCl$_3$), δ 13.01 (brs, 1H), 8.30 (d, 1H), 7.54 (d, 1H), 7.35 (t, 1H), 7.20 (t, 1H), 7.10 (d, 1H), 4.54 (dtt, 1H), 3.12 (brd, 2H), 2.60–2.40 (m, 5H including 2.53, s, 3H), 2.10–1.90 (m, 3H), 1.60–1.35 (m, 3H), 1 15–1.00 (m, 2H).

EXAMPLE 3

1-Methyl-3-indazolecarboxylic acid (endo-8-methyl-8-azabicyclo[3,2,1]oct-3-yl)ester monohydrochloride (E3)

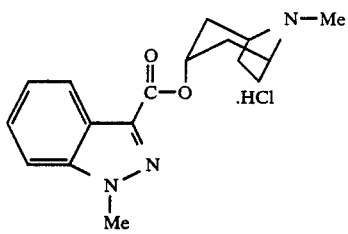

Following the procedure outlined in Example 1, the potassium salt of tropine (0.37 g) was reacted with 1-methyl-3-indazolcarboxylic acid chloride (0.21 g) to give, after treatment with ethanolic hydrogen chloride, the title compound (E3) (0.21 g) m.p. 257°–260° C.

$^1$H NMR (79.5 MHz, CDCl$_3$), δ 8.30–8.10 (m, 1H), 7.60–7.20 (m, 3H), 5.55–5.30 (m, 1H), 4.18 (s, 3H), 4.00–3.70 (m, 2H), 3.40–2.00 (m, 11H including 2.83, s, 3H).

Following the procedure outlined in Example 2, the following compounds were prepared:

EXAMPLE 4

N-(Endo-9-methyl-9-azabicyclo[3,3,1]non-3-yl)-5-fluoroindazole-3-carboxamide (E4)

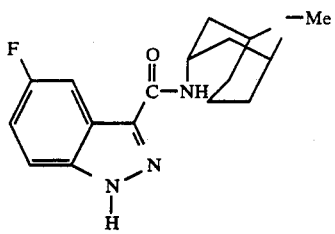
(E4)

m.p. 264°–267° C. (dec.)

$^1$H NMR (79.5 MHz, CDCl$_3$+(CD$_3$)$_2$SO), δ 13.30 (brs, 1H), 7.92 (dd. 1H), 7.53 m, 1H), 7.30–6.95 (m, 2H), 4.80–4.20 (m, 1H), 3.30–2.90 (m, 2H), 2.70–2.80 (m, 13H including 2.52, s, 3H).

EXAMPLE 5

N-(Endo-9-methyl-9-azabicyclo[3,3,1]non-3-yl)-5-chloroindazole-3-carboxamide (E5)

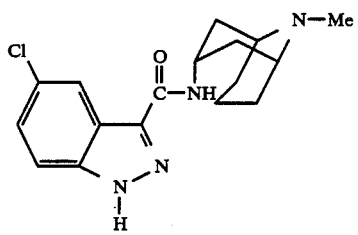
(E5)

$^1$H NMR (79.5 MHz, CDCl$_3$+(CD$_3$)$_2$SO), δ 13.50 (brs, 1H), 8.25 (brs, 1H), 7.80–7.25 (m, 3H), 4.75–4.20 (m, 1H), 3.50–2.80 (m, 2H), 2.65–0.80 (m, 13H including 2.49, s, 3H).

EXAMPLE 6

N-(Endo-9-methyl-9-azabicyclo[3,3,1]non-3-yl)-1-methylindazole-3-carboxamide monohydrochloride (E6)

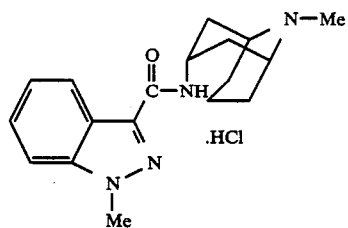
(E6)

A stirred solution of 1-methylindazole-3-carboxylic acid chloride (0.77 g) in dichloromethane (50 ml) was treated with a solution of endo-9-methyl-9-azabicyclo[3,3,1]nonan-3-amine (0.7 g) and triethylamine (0.7 ml) in dichloromethane (30 ml). After 2 h, the reaction mixture was washed with saturated aqueous NaHCO$_3$ (100 ml) and dried (K$_2$CO$_3$). The oil remaining after evaporation of the solvent was purified by column chromatography (TLC-alumina, CHCl$_3$) and treated with hydrogen chloride to give the title compound E6. m.p. 290°–292° C.

$^1$H NMR (270 MHz, CDCl$_3$), δ8.30 (d, 1H), 7.50–7.20 (m, 4H), 4.80–4.50 (m, 1H), 4.12 and 4.10 (2-s, 3H), 3.75–3.55 (m, 2H), 2.99 and 2.91 (2-s, 3H), 2.82–2.40 (m, 4H), 2.20–2.00 (m, 2H), 1.90–1.60 (m, 4H).

Following the procedure outlined in Example 6, the following compounds were prepared:

EXAMPLE 7

N-(Endo-9-methyl-9-azabicyclo[3,3,1]non-3-yl)-1-ethylindazole-3-carboxamide (E8)

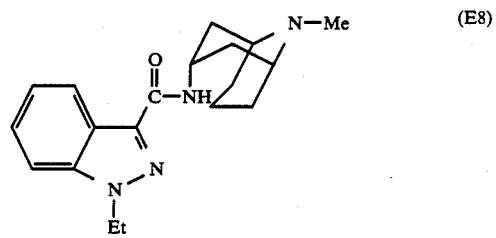
(E8)

$^1$H NMR (79.5 MHz, CDCl$_3$), δ8.42 (dm, 1H), 7.55–7.10 (m, 3H), 6.80 (brd, 1H), 4.80–4.20 (m, 3H including 4.42, q, 2H), 3.30–2.90 (m, 2H), 2.75–2.30 (m, 5H including 2.55, s, 3H), 2.20–0.90 (m, 11H including 1.54, t, 3H).

EXAMPLE 8

N-(Endo-9-methyl-9-azabicyclo[3,3,1]non-3-yl)-1,2-benzisoxazole-3-carboxamide (E9)

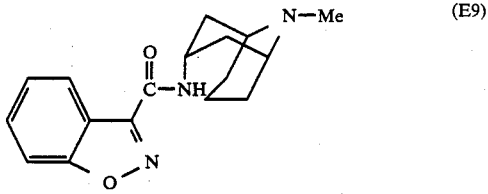
(E9)

m.p. 126°–128° C.

$^1$H NMR (79.5 MHz, CDCl$_3$) δ 8.35 (dm, 1H), 7.80–7.25 (m, 3H), 6.80 (brd, 1H), 4.80–4.30 (m, 1H), 3.35–3.00 (m, 2H), 2.80–2.25 (m, 5H including 2.56, s, 3H), 2.20–0.90 (m, 8H).

EXAMPLE 9

5α-N-(2-methyl-2-azabicyclo[2,2,2]oct-5-yl)-1-methyl-indazole-3-carboxamide (E10)

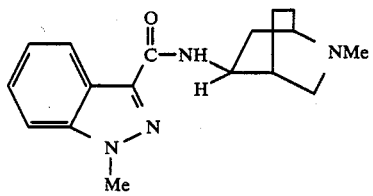
(E10)

$^1$H NMR (270 MHz, CDCl$_3$), δ 8.36 (dm, 1H), 7.50–7.49 (m, 2H), 7.33–7.24 (m, 1H), 7.05 (brd, 1H), 4.48–4.35 (m, 1H), 4.10 (s, 3H), 2.90 (brs, 2H), 2.76–2.60 (m, 2H), 2.45 (s, 3H), 2.15–2.00 (m, 2H), 1.95–1.80 (m, 1H), 1.71–1.55 (m, 2H), 1.44–1.34 (m, 1H).

EXAMPLE 10

N-(Exo-2-methyl-2-azabicyclo[2,2,1]hept-5-yl)-1-methylindazole-3-carboxamide monohydrochloride (E11)

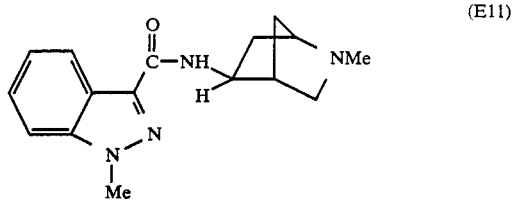

$^1$H NMR (270 MHz, CDCl$_3$), δ 13.00–12.50 (m, 1H), 8.28 (d, 1H), 7.50–7.20 (m, 3H), 6.82 (brs, 1H), 5.10–4.60 (m, 1H), 4.20–3.70 (m, 4H including 4.09, s, 3H), 3.30–1.70 (m, 10H).

EXAMPLE 11

N-(Endo-2-methyl-2-azabicyclo[2,2,1]hept-5-yl)-1-methylindazole-3-carboxamide monohydrochloride (E12)

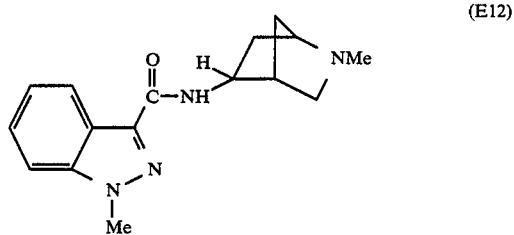

$^1$H NMR (270 MHz, CDCl$_3$), δ 12.40–12.10 (m, 1H), 8.40–8.20 (m, 2H), 7.50–7.20 (m, 3H), 4.72–4.55 (m, 1H), 4.22 (d, 1H), 4.13 (s, 3H), 3.80 (s, 1H), 3.21 (s, 1H), 3.00–2.85 (m, 4H including 2.80, s, 3H), 2.61 (d, 1H), 2.26 (t, 1H), 2.16–1.80 (m, 2H).

Pharmacology

Antagonism of the von Bezold-Jarisch reflex

The compounds were evaluated for antagonism of the von Bezold-Jarisch reflex evoked by 5-HT in the anaesthetised rat according to the following method:

Male rats 250–350 g, were anaesthetised with urethane (1.25 g/kg intraperitoneally) and blood pressure and heart rate recorded as described by Fozard J. R. et al., J. Cardiovasc. Pharmacol. 2, 229–245 (1980). A submaximal dose of 5-HT (usually 6 μg/kg) was given repeatedly by the intravenous route and changes in heart rate quantified. Compounds were given intravenously and the concentration required to reduce the 5 HT-evoked response to 50% of the control response (ED$_{50}$) was then determined.

The results were as follows.

| Compound No. | ED$_{50}$ (mg/kg) |
|---|---|
| E1 | 0.005 |
| E2 | 0.0011 |
| E3 | 0.0014 |
| E5 | 0.015 |
| E6 | 0.0007 |
| E8 | 0.0006 |
| E10 | 0.0017 |
| E11 | 0.01 |

I claim:

1. A compound of formula (I), or a pharmaceutically acceptable salt thereof:

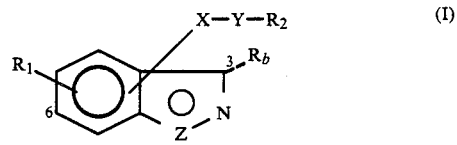

wherein

X is CO and Y is NH;

Z is NR$_3$ wherein R$_3$ is hydrogen, C$_{1-6}$ alkyl, C$_{3-7}$ alkenyl-methyl, phenyl or phenyl C$_{1-4}$ alkyl either of which phenyl moieties may be substituted by one or two of halogen, CF$_3$, C$_{1-6}$ alkoxy or C$_{1-6}$ alkyl;

R$_b$ is present when X-Y-R$_2$ is attached at the phenyl ring and is selected from hydrogen, halogen, CF$_3$, hydroxy, C$_{1-6}$ alkoxy or C$_{1-6}$ alkyl;

R$_1$ is hydrogen, halogen, CF$_3$, C$_{1-6}$ alkyl, C$_{1-6}$ alkoxy, C$_{1-6}$ alkylthio, C$_{1-7}$ acyl, C$_{1-7}$ acylamino, C$_{1-6}$ alkylsulphonylamino, N-(C$_{1-6}$ alkylsulphonyl)-N-C$_{1-4}$ alkylamino, C$_{1-6}$ alkylsulphinyl, hydroxy, nitro or amino, aminocarbonyl, aminosulphonyl, aminosulphonylamino or N-(aminosulphonyl)-C$_{1-4}$ alkylamino optionally N-substituted by one or two groups selected from C$_{1-6}$ alkyl, C$_{3-8}$ cycloalkyl, C$_{3-8}$ cycloalkyl C$_{1-4}$ alkyl, phenyl or phenyl C$_{1-4}$ alkyl groups or optionally N-disubstituted by C$_{4-5}$ polymethylene;

R$_2$ is a group of formula (a),

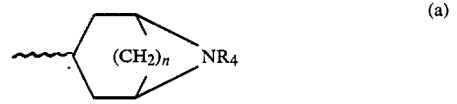

wherein n is 2 or 3; and

R$_4$ is C$_{1-7}$ alkyl, C$_{3-8}$ cycloalkyl, C$_{3-8}$ cycloalkyl-C$_{1-2}$ alkyl, or a group (CH$_2$)$_t$R$_6$ where t is 1 or 2 and R$_6$ is thienyl, pyrrolyl or furyl optionally substituted by one or two substituents selected from C$_{1-6}$ alkyl, C$_{1-6}$ alkoxy, trifluoromethyl or halogen, or is phenyl optionally substituted by one or two substituents selected from C$_{1-4}$ alkoxy, trifluoromethyl, halogen, nitro, carboxy, esterified carboxy, and C$_{1-4}$ alkyl optionally substituted by hydroxy, C$_{1-4}$ alkoxy, carboxy, esterified carboxy or in vivo hydrolysable acyloxy.

2. A compound according to claim 1 wherein n is 3.

3. A compound according to claim 1 wherein R$_3$ is hydrogen or methyl.

4. A compound according to claim 1 wherein the X-Y-R$_2$ side chain is attached at position 3, as depicted in formula (I) in claim 1.

5. A compound according to claim 1 wherein R$_1$ is hydrogen or 5-halo.

6. A compound according to claim 1 wherein R$_4$ is C$_{1-7}$ alkyl.

7. A compound according to claim 4 wherein $R_4$ is methyl.

8. A compound selected from the group consisting of:
N-(endo-9-methyl-9-azabicyclo[3.3.1]non-3-yl)-indazole-3carboxamide,
N-(endo-9-methyl-9-azabicyclo[3.3.1]non-3-yl)-5-fluoroindazole-3-carboxamide,
N-(endo-9-methyl-9-azabicyclo[3.3.1]non-3-yl)-5-chloroindazole-3-carboxamide,
N-(endo-9-methyl-9-azabicyclo[3.3.2]non-3-yl)-1-methylindazole-3-carboxamide,
N-(endo-9-methyl-9-azabicyclo[3.3.1]non-3-yl)-1-ethylindazole-3-carboxamide, and pharmaceutically acceptable salts of any of the foregoing.

9. A compound according to claim 1 wherein $Y-R_2$ is in the endo configuration.

10. N-(Endo-9-methyl-9-azabicyclo[3.3.1]non-3-yl)-1-methylindazole-3-carboxamide monohydrochloride.

11. A pharmaceutical composition for the treatment of migraine or cluster headache, comprising an effective amount of a compound according to claim 1 or a pharmaceutically acceptable salt thereof, and a pharmaceutically acceptable carrier.

12. A pharmaceutical composition for the treatment of trigeminal neuralgia, comprising an effective amount of a compound according to claim 1 or a pharmaceutically acceptable salt thereof, and a pharmaceutically acceptable carrier.

13. A pharmaceutical composition for the treatment of emesis, comprising an effective amount of a compound according to claim 1 or a pharmaceutically acceptable salt thereof, and a pharmaceutically acceptable carrier.

14. A method of treatment or prophylaxis of migraine or cluster headache in mammals, which comprises the administration to the mammal of an effective amount of a compound according to claim 1, or a pharmaceutically acceptable salt thereof.

15. A method of treatment or prophylaxis of trigeminal neuralgia in mammals, which comprises the administration to the mammal of an effective amount of a compound according to claim 1, or a pharmaceutically acceptable salt thereof.

16. A method of treatment or prophylaxis of emesis in mammals, which comprises the administration to the mammal of an effective amount of a compound according to claim 1, or a pharmaceutically acceptable salt thereof.

17. A method of treatment of anxiety in mammals, which comprises the administration to the mammal of an effective amount of a compound according to claim 1, or a pharmaceutically acceptable salt thereof.

18. A method of treatment of psychosis in mammals, which comprises the administration to the mammal of an effective amount of a compound according to claim 1, or a pharmaceutically acceptable salt thereof.

19. A pharmaceutical composition for the treatment of anxiety, comprising an effective amount of a compound according to claim 1, or a pharmaceutically acceptable salts thereof, and a pharmaceutically acceptable carrier.

20. A pharmaceutical composition for the treatment of psychosis, comprising an effective amount of a compond according to claim 1, or a pharmaceutically acceptable salt thereof, and a pharmaceutically acceptable carrier.

* * * * *

UNITED STATES PATENT AND TRADEMARK OFFICE

CERTIFICATE EXTENDING PATENT TERM
UNDER 35 U.S.C. § 156

PATENT NO.     : 4,886,808

DATED          : December 12, 1989

INVENTOR(S)    : Francis D. King

PATENT OWNER   : Beecham Group p.l.c.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

382 DAYS with all rights pertaining thereto as provided by 35 U.S.C. § 156(b).

I have caused the seal of the Patent and Trademark Office to be affixed this 23rd day of January 1996.

Bruce A. Lehman
Assistant Secretary of Commerce and
Commissioner of Patents and Trademarks

UNITED STATES PATENT AND TRADEMARK OFFICE
CERTIFICATE OF CORRECTION

PATENT NO. : 4,886,808
DATED : December 12, 1989
INVENTOR(S) : King

It is certified that error appears in the above-identified patent and that said Letters Patent is hereby corrected as shown below:

In column 17, lines 10 and 11, change "N-(endo-9-methyl-9-azabicyclo[3.3.2] non-3-yl)-1-methylindazole-3-carboxamide," to --- N-(endo-9-methyl-9-azabicyclo[3.3.1] non-3-yl)-1-methylindazole-3-carboxamide, ---.

Signed and Sealed this

Seventeenth Day of October, 2000

Attest:

Q. TODD DICKINSON

*Attesting Officer*     *Director of Patents and Trademarks*